United States Patent [19]

Sano et al.

[11] Patent Number: 5,393,876
[45] Date of Patent: Feb. 28, 1995

[54] PROCESS FOR PRODUCING MALTOOLIGOSACCHARIDE DERIVATIVES

[75] Inventors: Atsunori Sano; Satoshi Hashizume; Hiroyuki Tsurumoto, all of Kawagoe, Japan

[73] Assignee: Wako Pure Chemical Industries, Ltd., Osaka, Japan

[21] Appl. No.: 44,627

[22] Filed: Apr. 9, 1993

[30] Foreign Application Priority Data

Apr. 15, 1992 [JP] Japan .................................. 4-121303

[51] Int. Cl.$^6$ ..................... C07H 15/00; C07H 15/04
[52] U.S. Cl. .................................. 536/18.5; 536/1.11; 536/4.1; 536/18.6; 536/17.8; 536/17.9; 536/120; 536/124; 435/18; 435/22
[58] Field of Search .................... 536/18.5, 1.11, 4.1, 536/18.6, 17.8, 17.9, 120, 124; 435/18, 22

[56] References Cited

U.S. PATENT DOCUMENTS

| | | | |
|---|---|---|---|
| 4,172,765 | 10/1979 | Keyes | 435/22 |
| 4,405,816 | 9/1983 | Skaletz | 568/592 |
| 4,649,108 | 3/1987 | Blair | 435/22 |
| 4,932,871 | 6/1990 | Bell et al. | 435/22 |
| 4,987,067 | 1/1991 | Ishimaru et al. | 435/22 |
| 5,192,666 | 3/1993 | Ikenaka et al. | 435/22 |
| 5,264,345 | 11/1993 | Schmidt et al. | 435/22 |

*Primary Examiner*—Ronald W. Griffin
*Attorney, Agent, or Firm*—Armstrong, Westerman, Hattori, McLeland & Naughton

[57] ABSTRACT

A polyacyl maltooligosaccharide derivative which is a precursor of a maltooligosaccharide derivative having modified groups at the 6-position or 4- and 6-positions of non-reducing end glucose unit and being effectively used as a substrate for measuring α-amylase activity, can be produced under mild conditions by crosslinking OH groups in the non-reducing end glucose unit of oligosaccharide with a benzylidene group having an alkoxy group, followed by acylation and treatment with a dilute acid.

5 Claims, No Drawings

PROCESS FOR PRODUCING MALTOOLIGOSACCHARIDE DERIVATIVES

BACKGROUND OF THE INVENTION

This invention relates to a process for producing a maltooligosaccharide derivative very useful, for example, as a precursor of a maltooligosaccharide derivative having modified groups at the 6-position or the 4- and 6-positions of non-reducing end glucose unit which can be effectively used as a substrate for measuring α-amylase activity.

Measurement of α-amylase activity in samples, in particular, saliva, pancreatic juice, blood and urine in a human body gives an important indication for medical diagnoses. For example, in the case of pancreatitis, pancreas cancer and parotiditis, the level of α-amylase activity in blood and urine is much higher than its usual level. For the measurement, there has come to be generally employed in recent years a coupling enzyme method using as substrate a maltooligosaccharide derivative having a color-producing group at the reducing end and a non-reducing end glucose unit modified at the 6-position or the 4- and 6-positions.

In the synthesis of such a substrate having a non-reducing end glucose unit modified only at the 6-position or the 4- and 6-positions, if there is a common intermediate which permits free and easy introduction of various modifying groups only into the 6-position or the 4- and 6-positions of the non-reducing end glucose unit, it becomes possible to synthesize rapidly and efficiently a substrate for measuring α-amylase activity or an intermediate thereof, which has higher performance characteristics and a newer function. Therefore, the production and development of a substrate for measuring α-amylase activity proceed rapidly, and hence the common intermediate is of high utility value.

An example of the common intermediate is a polyacyl maltooligosaccharide derivative retaining the hydroxyl groups at the 4- and 6-positions of non-reducing end glucose unit. Employment of this intermediate permits selective and easy synthesis of a substrate having a non-reducing end glucose unit modified only in the hydroxyl group at the 6-position and a substrate having a non-reducing end glucose unit modified at the 4- and 6-positions with bridge type blocking groups. Moreover, since this intermediate is formed by acylation in all hydroxyl groups other than the hydroxyl groups at the 4- and 6-positions, it is highly lipophilic and is soluble in various organic solvents. Therefore, it has many advantages, for example, in that the determination of reaction reagents, reaction conditions and the like is easy.

As heretofore known processes for producing a polyacyl maltooligosaccharide derivative retaining the hydroxyl groups at the 4- and 6-positions, there are processes disclosed in Japanese Patent Unexamined Publication Nos. 60-54395 (U.S. Pat. Nos. 4,709,020, 4,818,692) and 2-49796 (U.S. Pat. No. 5,011,923), etc., namely, a process which uses as starting material a commercially available oligosaccharide derivative having an optically measurable group at the reducing end and comprises blocking the 4- and 6-positions of non-reducing end glucose unit with a cyclic ketal (or acetal) type blocking group such as ethylidene group, isopropylidene group, benzylidene group or the like, acylating the thus treated derivative, and then deblocking the 4- and 6-positions. This method, however, is disadvantageous in that both the blocking step and the deblocking step require severe conditions and a troublesome procedure and that the yield is low.

The reasons for the low yield in the case of the blocking with the aforesaid cyclic ketal (or acetal) type blocking groups are, for example, as follows. The introduction of the blocking groups is naturally not easy. Because of the severe conditions in both the blocking step and the deblocking step (particularly in the deblocking step), some of modifying groups at the non-reducing end are removed. Also in positions other than the 4- and 6-positions of non-reducing end glucose unit, blocking by crosslinking takes place in the same glucose unit or between two glucose units (Carbohyd. Res., 185, 91–104 (1989)).

In addition to the above process, there is the process disclosed in the specification of EP 0512808 in which the present inventors have applied for a patent. This process also cannot give a sufficient yield because a considerable amount of polyacyl maltooligosaccharide derivatives retaining the hydroxyl groups at positions other than the 4- and 6-positions are produced as by-products together with a polyacyl maltooligosaccharide derivative retaining the hydroxyl groups only at the 4- and 6-positions.

Accordingly, there is an eager desire for the advent of a process for producing a polyacyl maltooligosaccharide derivative retaining the hydroxyl groups only at the 4- and 6-positions of non-reducing end glucose unit, easily in high yield under mild conditions by using as starting material a commercially available oligosaccharide derivative having an optically measurable group at the reducing end.

SUMMARY OF THE INVENTION

This invention was made in view of such conditions and is intended to provide a process for producing a polyacyl maltooligosaccharide derivative which permits free introduction of various modifying groups into the 6-position or the 4- and 6-positions of non-reducing end glucose unit, easily in high yield under mild conditions.

This invention provides a process for producing a maltooligosaccharide derivative represented by the formula:

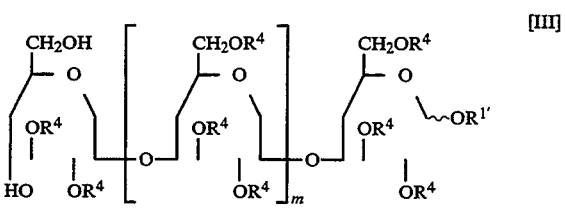

wherein $R^{1'}$ is an optically measurable group or an acyl group; $R^4$ is an acyl group; and m is an integer of 1 to 5; which comprises reacting a compound represented by the formula:

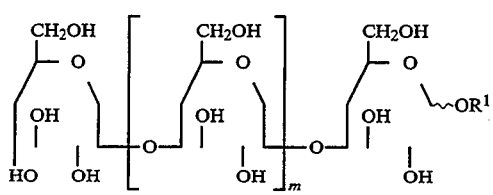

wherein $R^1$ is an optically measurable group or a hydrogen atom; and m is as defined above, with a compound represented by the formula:

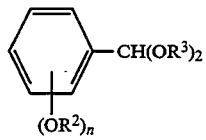

wherein $R^2$ is a lower alkyl group; $R^3$ is a lower alkyl group; and n is an integer of 1 to 3, to block the hydroxyl groups at the 4- and 6-positions of non-reducing end glucose unit of the compound of the formula [I] by their crosslinking with a benzylidene group having an alkoxy group(s), acylating the reaction product, and then treating the acylated product with a dilute acid.

DESCRIPTION OF THE PREFERRED EMBODIMENTS

According to this invention, when a compound of the formula:

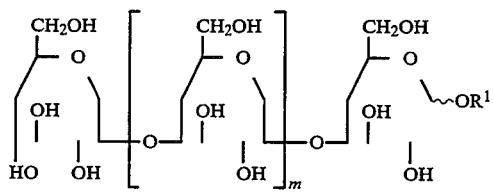

wherein $R^1$ and m are as defined above, is reacted with a compound of the formula:

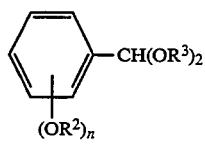

wherein $R^2$, $R^3$ and n are as defined above, the hydroxyl groups at the 4- and 6-positions of non-reducing end glucose unit of the compound of the formula [I] are blocked by crosslinking with a benzylidene group having an alkoxy group(s), preferentially and easily in high yield. The benzylidene group having an alkoxy group can be removed efficiently under very mild conditions and is much easier to remove than 4- and 6-positions bridge type blocking groups such as ethylidene group, isopropylidene group, benzylidene group or the like which have been conventionally used. Therefore, a compound of the formula:

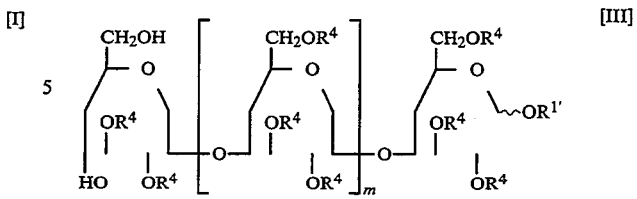

wherein $R^{1'}$, $R^4$ and m are as defined above, can be produced in high yield. Furthermore, the benzylidene group having an alkoxy group is very stable to acylation conditions like the conventional 4- and 6-positions bridge type blocking groups.

In the formulas [I] and [III], as the optically measurable group represented by $R^1$ or $R^{1'}$, any group may be used so long as it is releasable from a glucoside form by the action of an enzyme such as glucoamylase-[E.C.3.2.1.3.], α-glucosidase-[E.C.3.2.1.20.], β-glucosidase[E.C.3.2.1.21.], isomaltase[E.C.3.2.1.10.] or β-amylase[E.C.3.2.1.2.], and in addition after being released, it has any one of the following properties: it can absorb a visible light or an ultraviolet light in itself like nitrophenol or derivatives thereof; it can emit fluorescence in itself. like substituted or unsubstituted umbelliferone and derivatives thereof; it is coupled to a coupler by the action of an oxidase such as catechol oxidase, laccase, tyrosinase or monophenol oxidase to form a dye; it is coupled to a coupler by an oxidizing agent to form a dye.

Typical examples of the optically measurable group are unsubstituted aryl groups such as phenyl, 1-naphthyl, 2-methylphenyl, 2-methyl-1-naphthyl, etc.; substituted aryl groups such as 4-nitrophenyl, 3-nitrophenyl, 2-chlorophenyl, 4-chlorophenyl, 2,6-dichlorophenyl, 2-chloro-4-nitrophenyl, 2,6-dichloro-4-nitrophenyl, 2-methoxyphenyl, 4-methoxyphenyl, 2-carboxyphenyl, 2-sulfophenyl, 2-sulfo-1-naphthyl, 2-carboxy-1-naphthyl, etc.; unsubstituted umbelliferyl group; substituted umbelliferyl groups such as 4-methylumbelliferyl, 4-trifluoromethylumbelliferyl, etc.; unsubstituted indoxyl group; and substituted indoxyl groups such as 5-bromoindoxyl, 4-chloro-3-bromoindoxyl, etc.

$R^1$ in the formula [I] includes hydrogen atom in addition to these optically measurable groups. $R^{1'}$ in the formula [III] includes acyl groups in addition to the optically measurable groups.

As the acyl groups represented by $R^4$ and $R^{1'}$ in the formula [III], there can be exemplified aliphatic acyl groups such as acetyl, monochloroacetyl, trichloroacetyl, trifluoroacetyl, propionyl, butyryl, levulinoyl, etc.; andaromatic acyl groups such as benzoyl, p-methoxybenzoyl, etc. Usually, there can be preferably exemplified acetyl group and benzoyl group which are obtained from inexpensive and easily available reagents.

In the formulas [I] and [III], m is an integer of 1 to 5. That is, the compounds of the formulas [I] and [III] are derivatives of maltotriose, maltotetraose, maltopentaose, maltohexaose or maltoheptaose.

In the formula [II], the lower alkyl group represented by each of $R^2$ and $R^3$ includes, for example, alkyl groups having 1 to 6 carbon atoms (e.g. methyl group, ethyl group, propyl group, butyl group, pentyl group and hexyl group) which may be linear, branched or cyclic. Although the position of substitution by the $OR^2$ group may be any position, it is particularly preferably the p-position which is superior in ease of blocking and deblocking, stability, etc. Although the number of the $OR^2$ groups (=n) may be any of 1, 2 and 3, it is particularly preferably 1 for the same reason as described above.

The compound of the formula [II] is an alkoxy-substituted benzaldehyde dialkylacetal derivative and specific examples thereof are o-anisaldehyde dimethylacetal, m-anisaldehyde dimethylacetal, p-anisaldehyde dimethylacetal, p-anisaldehyde diethylacetal, p-acetaldehyde diethylacetal, p-acetaldehyde diisopropylacetal, veratrum aldehyde dimethylacetal, veratrum aldehyde diethylacetal, 3,4,5-trimethoxybenzaldehyde dimethylacetal, 3,4,5-trimethoxybenzaldehyde diethylacetal, etc. All of these compounds can easily be synthesized according to the method described in S.R. Sandler et. al.; Organic Functional Group Preparation Vol. III, p 34 (ACADEMIC PRESS New York and London).

The present invention's process for producing the compound of the formula:

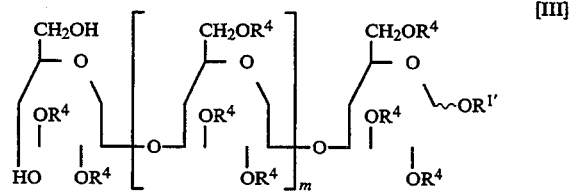

wherein $R^{1'}$, $R^4$ and m are as defined above (hereinafter abbreviated as "compound (III)") is practiced substantially as follows.

First, a compound of the formula:

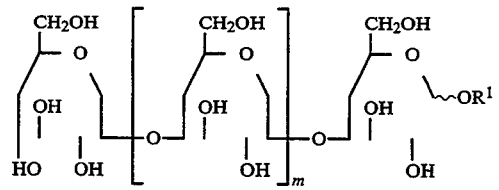

wherein $R^1$ and m are as defined above (hereinafter abbreviated as "compound (I)") is reacted with a compound of the formula:

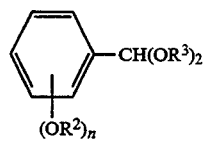

wherein $R^2$, $R^3$ and n are as defined above (hereinafter abbreviated as "compound (II)") to obtain a compound of the formula:

droxyl groups at the 4- and 6-positions of non-reducing end glucose unit have been blocked by cross-linking with a benzylidene group having an alkoxy group(s).

Specific examples of the compound (I) used here are relatively generally used compounds such as p-nitrophenylmaltotrioside, p-nitrophenylmaltotetraoside, p-nitrophenylmaltopentaoside, p-nitrophenylmaltohexaoside, p-nitrophenylmaltoheptaoside, etc. As these compounds, commercially available ones may be used as they are. When the compounds are not on the market, they may be synthesized according to, for example, the method described in Carbohydr. Res., 61, 359–368 (1978), Japanese Patent Unexamined Publication No. 53-12831 (GB 1,570,152), etc.

Although it is sufficient that the reaction of the compound (I) with the compound (II) is carried out merely by mixing them without a solvent or in a solvent capable of dissolving the compound (I), employment of an acid catalyst is preferable because it improves the reaction rate markedly. As the acid catalyst, there can be exemplified acids generally used as acid catalysts, such as hydrochloric acid, sulfuric acid, p-toluenesulfonic acid, etc. The reaction can be carried out more effectively by eliminating a by-produced alcohol by a procedure such as distilling-off under reduced pressure. The compound (II) is used usually in an amount of about 1 to about 10 moles, preferably 1 to 2 moles, per mole of the compound (I). A solvent for the reaction is not always necessary. When it is used, solvents capable of dissolving the compound (I), for example, N,N-dimethylformamide (DMF), dimethylacetamide (DMAC) and dimethyl sulfoxide (DMSO) are preferable. As to the reaction temperature, the reaction can be carried out in a wide temperature range of from room temperature to with heating. Usually, the reaction is carried out preferably with heating at approximately 40°–90° C. Although the reaction time, as a matter of course, varies depending on the reaction temperature, the solvent and other conditions, it is usually 10 minutes to 30 hours or more, preferably 3 to 8 hours. It is sufficient that the progress of the reaction is followed by an analytical means such as TLC, NMR or the like.

In the above reaction of the compound (I) with the compound (II), an aldehyde form which is a starting compound for a compound of the formula [II] can be directly used in place of the compound (II), but in this case, the reaction conditions become a little severer.

The compound (IV) thus obtained is then acylated. For the acylation, the reaction solution can be subjected to acylation reaction without isolating the compound (IV). Needless to say, the compound (IV) may be once isolated by a column chromatography or the like, but in this case, a troublesome procedure is required. Therefore, it is preferable to carry out the acylation without the isolation.

When the compound (IV) is acylated, there is obtained a compound of the formula:

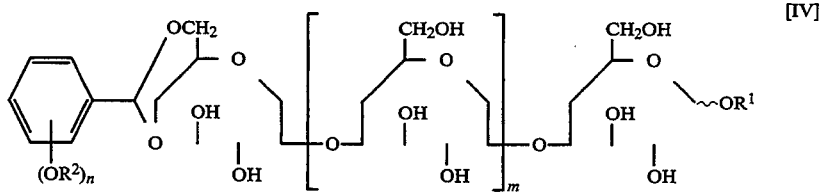

wherein $R^1$, $R^2$, m and n are as defined above (hereinafter abbreviated as "compound (IV)") in which the hy-

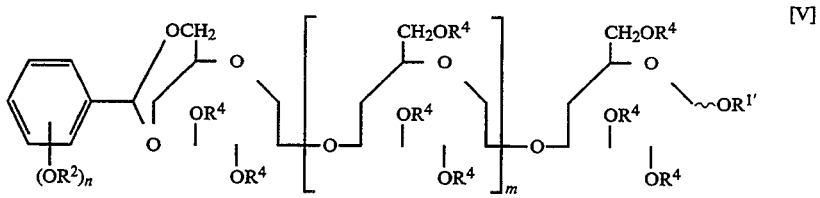

wherein $R^{1'}$, $R^2$, $R^4$, m and n are as defined above (hereinafter abbreviated as "compound (V)"). It is sufficient that the acylation reaction is carried out in the presence of a base such as pyridine, dimethylaminopyridine or the like by a conventional method at a temperature of ice cooling to 100° C. preferably 0° to 50° C. by using acetic anhydride, acetyl chloride, benzoyl chloride or the like as an acylating agent. Thus, the compound (V) can easily be produced.

Like the compound (IV), the compound (V) need not be isolated from the acylation reaction solution. When a dilute acid such as diluted hydrochloric acid or diluted sulfuric acid which has a concentration of 1% to 15% is poured into this reaction solution at a temperature of 0° to 50° C., preferably 0° to 30° C., e.g. room temperature, the surplus acylating agent can be decomposed and at the same time, the bridge type blocking group for the hydroxyl groups at the 4- and 6-positions of non-reducing end glucose unit can be decomposed, whereby the desired compound (III) can be obtained. After completion of this reaction, the desired compound is isolated by a conventional after-treatment, for example, as follows. When the end product is obtained as crystals, it is collected by filtration. When the end product is obtained as an oily substance, it is extracted with a suitable organic solvent such as chloroform, methylene chloride, ethyl acetate, toluene or the like.

The bridge type blocking group for the hydroxyl groups at the 4- and 6-positions of non-reducing end glucose unit can be removed to obtain the desired compound (III), also by adding water to the acylation reaction solution to decompose the surplus acylating agent after completion of the acylation reaction, extracting the compound (V) with a suitable organic solvent such as chloroform, methylene chloride, ethyl acetate, toluene or the like, and then washing the extracted solution with the same dilute acid as described above (diluted hydrochloric acid, diluted sulfuric acid, etc.). In this case, the desired compound (III) can be isolated merely by distilling off the extraction solvent.

The compound (III) obtained in the manner described above is contaminated in some cases with peracyl maltooligosaccharide derivatives formed by acylation also in the hydroxyl groups at the 4- and 6-positions of non-reducing end glucose unit. Although these derivatives may, if necessary, be separated by column chromatography, recrystallization, etc. to purify the compound (III), a mixture of the compound (III) and the derivatives is usually usable as it is without any trouble, for producing, for example, a substrate for measuring α-amylase activity which has modified groups at the 6-position or 4- and 6-positions of non-reducing end glucose unit. Therefore, when the compound (III) is used for such a purpose, the derivatives need not be particularly separated to purify the compound (III).

For blocking the hydroxyl groups at the 4- and 6-positions of non-reducing end glucose unit of the compound (I), blocking groups such as ethylidene group, isopropylidene group, benzylidene group, etc. have heretofore been generally used. When removed, these blocking groups require a reaction under severe conditions, for example, a reaction in acetic acid with heating under reflux, or a reaction in concentrated hydrochloric acid with stirring for several hours. Therefore, in conventional methods using these bridge type blocking groups, a polyacyl maltooligosaccharide derivative having the blocked 4- and 6-positions should be once isolated when the bridge type blocking group at the 4- and 6-positions is removed. Therefore, the yield is low and moreover a troublesome procedure is required. This has been one of the defects of the conventional methods. On the other hand, the bridge type blocking group used in this invention can be removed under mild conditions. Therefore, in the process of this invention, the intermediate obtained in the preceding step need not be isolated not only before the acylation but also before the deblocking, so that the compound (III) can be synthesized by a one-pot reaction, resulting in a greatly simplified procedure.

It can be speculated that the reason why the bridge type blocking group used in this invention requires only easy blocking step and deblocking step and gives a high yield is that the electron-donating properties of the alkoxy group ($R^2O$ group) as substituent on the benzene ring of the benzylidene group increase the reactivity of the acetal portion. Accordingly, the bridge type blocking group used in this invention can be said to be strikingly different in this point from the ethylidene group, isopropylidene group, benzylidene group and the like which are considered to be essentially poor in such an effect.

By replacing the hydroxyl group at the 6-position or the hydroxyl groups at the 4- and 6-positions of the maltooligosaccharide derivative of the formula [III] obtained by the process of this invention, by a modifying group other than acyl group and deacylating the thus treated derivative, there can very easily be synthesized various maltooligosaccharide derivatives having modified groups at the 6-position or 4- and 6-positions of non-reducing end glucose unit and an optically measurable group at the reducing end which are useful as substrates for measuring α-amylase activity.

Examples are described below but they are not intended in any way to limit the scope of this invention.

EXAMPLE 1

Synthesis of 4-nitrophenyl O-(2,3-di-O-acetyl-α-D-glucopyranosyl)-(1→4)-O-(2,3,6-tri-O-acetyl-α-D-glucopyranosyl)-(1→4)-O-(2,3,6-tri-O-acetyl-α-D-glucopyranosyl)-(1→4)-O-(2,3,6-tri-O-acetyl-α-D-glucopyranosyl)-(1→4)-O-2,3,6-tri-O-acetyl-α-D-glucopyranoside (hereinafter abbreviated as "G5P(Ac)14")

In 50 ml of N,N-dimethylformamide (DMF) were dissolved 4.75 g of 4-nitrophenyl O-α-D-glucopyranosyl-(1→4)-O-α-D-glucopyranosyl-(1→4)-O-α-D -glucopyranosyl-(1→4)-O-α-D-glucopyranosyl-(1→4)-O-α-D-glucopyranoside (hereinafter abbreviated as "G5P") and 1.8 g of p-anisaldehyde dimethylacetal, followed by adding thereto 190 mg of p-toluenesulfonic acid, and the reaction was carried out at 40°–50° C. under a vacuum of 100–200 Torr. After completion of the reaction, 100 ml of pyridine and 40 ml of acetic anhydride were added to the reaction solution, and stirred overnight at room temperature. To the thus obtained reaction solution was added 20 ml of 10% hydrochloric acid, and stirred overnight at room temperature, after which the resulting reaction solution was poured into ice water and stirred for 3 hours. The crystals thus precipitated were collected by filtration, washed with water, and then dried under reduced pressure to obtain 7.3 g of white crystals. Yield of the crude product: 94%. The G5P(Ac)$_{14}$ content of the white crystals was about 64%. Then, the white crystals were purified by a column chromatography [packing: Wako-gel C-200 (a trade name, Wako Pure Chemical Industries, Ltd.), eluent: 1,2-dichloroethane-acetone (4: 1)] to obtain 4.5 g of purified G5P(Ac)$_{14}$. Yield: 58%.

IR (KBr, cm$^{-1}$): 3400, 1720, 1240, 1040
NMR (270MHz, CDCl$_3$):
1.9–2.2 (42H, CH$_3$), 3.4–5.8 (3H, CH, CH$_2$, OH), 7.2–7.3 (2H, arom-H), 8.2–8.3 (2H, atom-H)

EXAMPLE 2

Synthesis of G5P(Ac)$_{14}$

There was obtained 6.37 g of crude G5P(Ac)$_{14}$ in exactly the same manner as in Example 1 except for using veratrum aldehyde dimethylacetal in place of p-anisaldehyde dimethylacetal. Yield of the crude product: 82%. The G5P(Ac)$_{14}$ content of the crude product was about 52%.

EXMAPLE 3

Synthesis of G5P(Ac)$_{14}$

There was obtained 6.68 g of crude G5P(Ac)$_{14}$ in exactly the same manner as in Example 1 except for using 3,4,5-trimethoxybenzaldehyde dimethylacetal in place of p-anisaldehyde dimethylacetal. Yield of the crude product: 86%. The G5P(Ac)$_{14}$ content of the crude product was about 43%.

EXMAPLE 4

Synthesis of 2-chloro-4-nitrophenyl O-(2,3-di-O-acetyl-α-D-glucopyranosyl)-(1→4)-O-(2,3,6-tri-O-acetyl-α-D-glucopyranosyl)-(1→4)-O-(2,3,6-tri-O-acetyl-α-D-glucopyranosyl)-(1→4)-O-(2,3,6-tri-O-acetyl-α-D-glucopyranosyl)-(1→4)-O-2,3,6-tri-O-acetyl-α-D-glucopyranoside (hereinafter abbreviated as "G5CNP(Ac)$_{14}$")

White crystals of crude G5CNP(Ac)$_{14}$ were obtained in exactly the same manner as in Example 1 except for using 2-chloro-4-nitrophenyl O-α-D-glucopyranosyl-(1→4)-O-α-D-glucopyranosyl-(1→4)-O-α-D-glucopyranosyl-(1→4)-O-α-D-glucopyranosyl-(1→4)-O-α-D-glucopyranoside (hereinafter abbreviated as "G5CNP") in place of G5P. Yield of the crude product: 74%. The G5CNP(Ac)$_{14}$ content of the crude product was about 58%.

IR (KBr, cm$^{-1}$): 3500, 1760, 1240, 1040
NMR (270MHz, CDCl$_3$):
1.9–2.2 (42H, CH$_3$), 3.4–5.8 (37H, CH, CH$_2$, OH), 7.3 (1H, atom-H), 8.1 (1H, atom-H), 8.3 (1H, arom-H)

EXAMPLE 5

Synthesis of O-(2,3-di-O-acetyl-α-D-glucopyranosyl)-(1→4)-O-(2,3,6-tri-O-acetyl-α-D-glucopyranosyl)-(1→4)-O-(2,3,6-tri-O-acetyl-α-D-glucopyranosyl)-(1→4)-O-(2,3,6-tri-O-acetyl-α-D-glucopyranosyl)-(1→4)-O -(2,3,6-tri-O-acetyl-α-D-glucopyranosyl)-(1→4)-O-1,2,3,6-tetra-O-acetyl-α-D-glucopyranoside (hereinafter abbreviated as "G6(Ac)$_{18}$")

White crystals of crude G6(Ac)$_{18}$ were obtained in exactly the same manner as in Example 1 except for using O-α-D-glucopyranosyl-(1→4)-O-α-D-glucopyranosyl-(1→4)-O-α-D-glucopyranosyl-(1→4)-O-α-D-glucopyranosyl-(1→4)-O-α-D-glucopyranosyl-(1→4)-O-α-D-glucopyranose (hereinafter abbreviated as "G6") in place of G5P. Yield of the crude product: 64%. The G6(Ac)$_{18}$ content of the crude product was about 57%.

IR (KBr, cm$^{-1}$): 3400, 1760, 1230, 1040
NMR (270MHz, CDCl$_3$):
1.9–2.2 (54H, CH$_3$), 3.09–5.4 (43H, CH, CH$_2$, OH), 5.7 and 6.2 (1H, H-1)

This inventionsprovides a novel process for producing a polyacyl maltooligosaccharide derivative retaining the hydroxyl groups at the 4- and 6-positions of non-reducing end glucose unit which is a useful intermediate material for producing a substrate for measuring α-amylase activity. The process of this invention is markedly effective in that it can be applied without any trouble even when a maltooligosaccharide having a color-producing group attached to the reducing end glucose unit which group is easily releasable under acidic conditions is used as a starting material, and that it makes it possible to synthesize said polyacyl maltooligosaccharide derivative by one pot easily in high yield from a commercially available maltooligosaccharide having an optically measurable group at the reducing end. Thus, this invention contributes greatly to the development of a substrate for measuring α-amylase activity.

What is claimed is:

1. A process for producing a maltooligosaccharide glucoside of the formula

[III]

[structural formula of maltooligosaccharide with CH$_2$OH, CH$_2$OR$^4$, OR$^4$, HO, OR$^{1'}$ groups, repeating unit m]

wherein R$^{1'}$ is an acyl group or an optically measurable group releasable from the maltooligosaccharide glucoside by action of an enzyme and which, after being released, absorbs visible or ultraviolet light, is fluorescent, or forms a dye when coupled to a coupler by action of an oxidase or an oxidizing agent; R$^4$ is an acyl group and m is an integer of 1 to 5;

which comprises reacting a glucoside compound of the formula with a compound of the formula

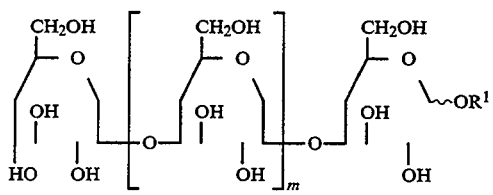

wherein $R^1$ is hydrogen or an optically measurable group which is releasable from the glucoside compound by action of an enzyme and which, after being released, absorbs visible or ultraviolet light, is fluorescent, or forms a dye when coupled to a coupler by action of an oxidase or an oxidizing agent; and m is as defined above; with a compound of the formula

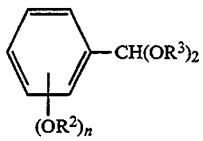

wherein $R^2$ is a lower alkyl group, $R^3$ is a lower alkyl group and n is an integer of 1 to 3, to form a cyclic acetal blocking the hydroxyl groups at the 4- and 6-positions of non-reducing end of the glucoside compound of formula; acylating the cyclic acetal reaction product and then decomposing the cyclic acetal with a dilute acid.

2. A process according to claim 1, wherein the reaction of the compound of the formula with the compound of the formula is carried out using an acid catalyst.

3. A process according to claim 1, wherein the acylation is carried out in the presence of a base using as an acylating agent acetic anhydride, acetyl chloride or benzoyl chloride.

4. A process according to claim 1, wherein the compound of the formula is p-anisaldehyde dimethylacetal, veratrum aldehyde dimethylacetal or 3,4,5-trimethoxybenzaldehyde dimethylacetal.

5. A process according to claim 1, wherein the compound of the formula is p-anisaldehyde dimethylacetal.

* * * * *

UNITED STATES PATENT AND TRADEMARK OFFICE
CERTIFICATE OF CORRECTION

PATENT NO. : 5,393,876
DATED : February 28, 1995
INVENTOR(S) : SANO et al.

It is certified that error appears in the above-indentified patent and that said Letters Patent is hereby Column 2, lines 55-63, formula [III] should read as follows:

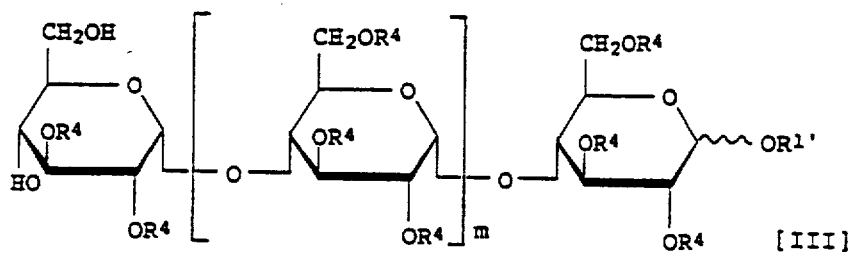

Column 3, lines 1-9, formula [I] should read as follows:

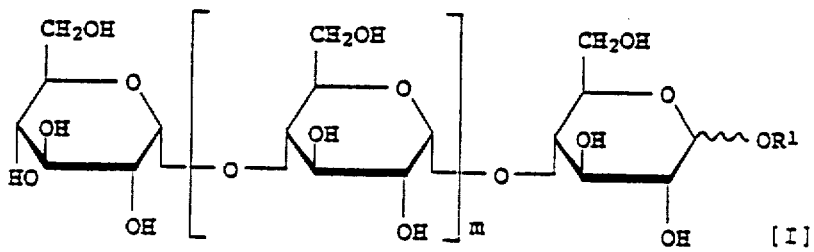

Column 3, lines 36-44, formula [I] should read as follows:

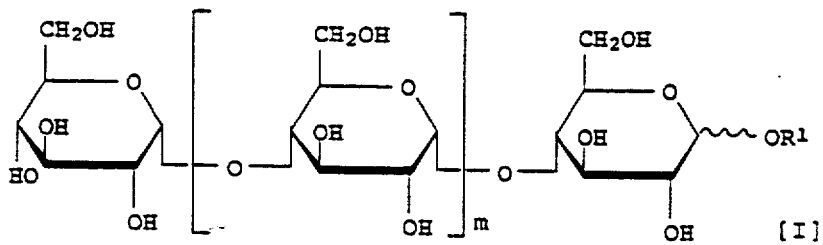

UNITED STATES PATENT AND TRADEMARK OFFICE
CERTIFICATE OF CORRECTION

PATENT NO. : 5,393,876
DATED : February 28, 1995
INVENTOR(S) : SANO et al

It is certified that error appears in the above-indentified patent and that said Letters Patent is hereby corrected as shown below:

Column 4, lines 1-9, formula [III] should read as follows:

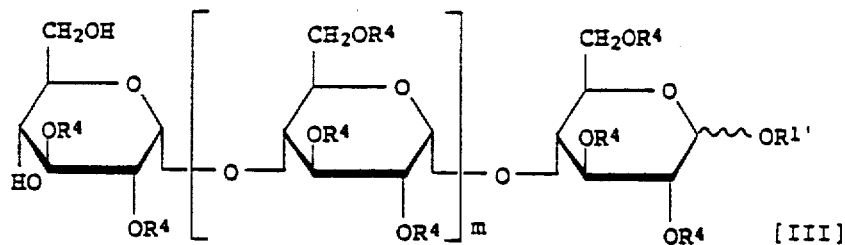

Column 5, lines 21-29, formula [III] should read as follows:

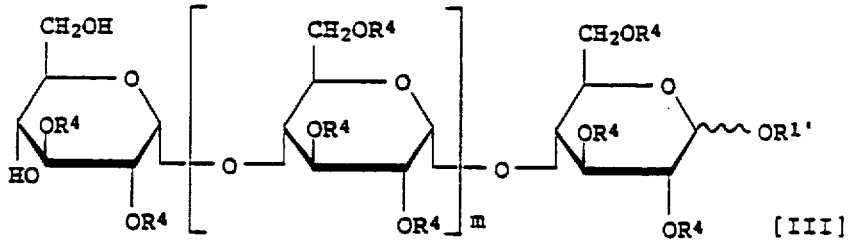

UNITED STATES PATENT AND TRADEMARK OFFICE
CERTIFICATE OF CORRECTION

PATENT NO. : 5,393,876
DATED : February 28, 1995
INVENTOR(S) : SANO et al

Page 3 of 5

It is certified that error appears in the above-indentified patent and that said Letters Patent is hereby corrected as shown below:

Column 5, lines 35-43, formula [I] should read as follows:

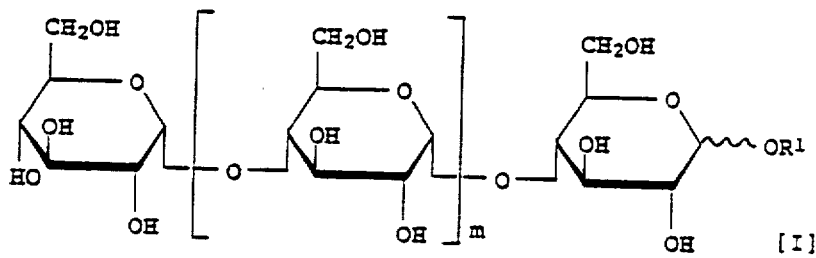

Column 5-6, lines 57-65, formula [IV] should read as follows:

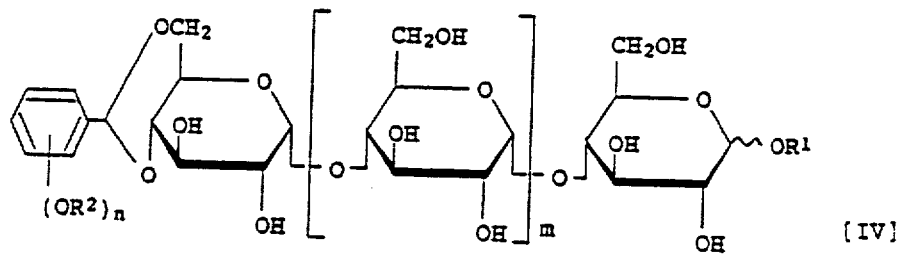

UNITED STATES PATENT AND TRADEMARK OFFICE
CERTIFICATE OF CORRECTION

PATENT NO. : 5,393,876
DATED : February 28, 1995
INVENTOR(S) : SANO et al

It is certified that error appears in the above-indentified patent and that said Letters Patent is hereby corrected as shown below:

Columns 7-8, lines 1-9, formula [V] should read as follows:

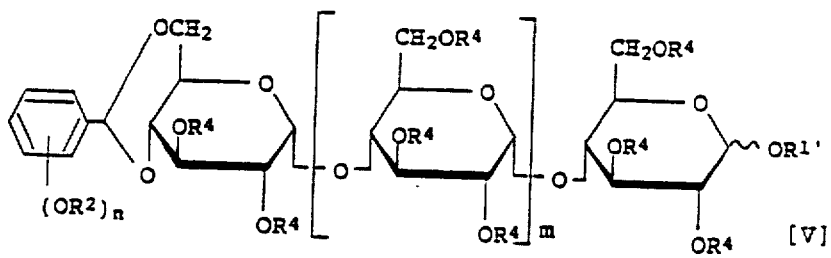

Column 10, lines 50-58, formula [III] should read as follows:

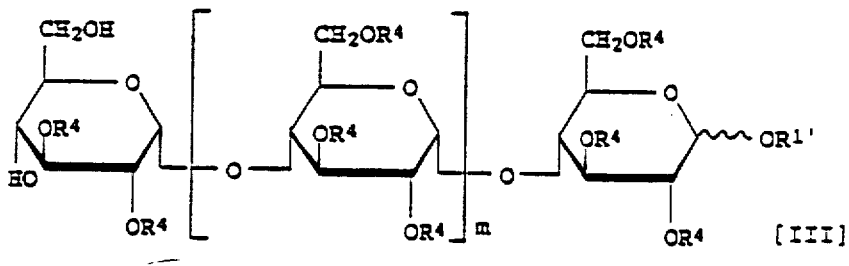

UNITED STATES PATENT AND TRADEMARK OFFICE
CERTIFICATE OF CORRECTION

PATENT NO. : 5,393,876
DATED : February 28, 1995
INVENTOR(S) : SANO et al

It is certified that error appears in the above-indentified patent and that said Letters Patent is hereby corrected as shown below:

Column 11, lines 5-12, formula [I] should read as follows:

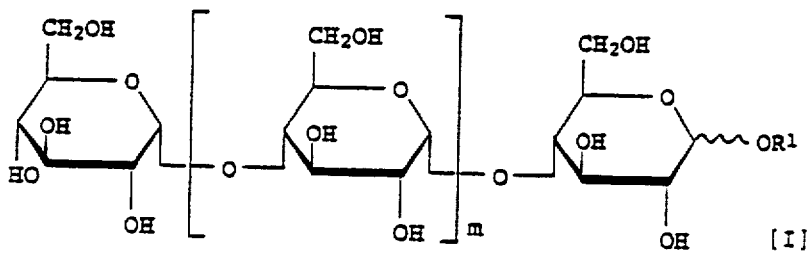

Column 12, line 13, after "formula" insert --[I]--, line 17, after "formula" insert --[I]--, line 18, after "formula" insert --[II]--, line 25, after "formula" insert --[II]--, line 29, after "formula" insert --[II]--.

Signed and Sealed this

Eighth Day of August, 1995

Attest:

BRUCE LEHMAN

*Attesting Officer*      *Commissioner of Patents and Trademarks*